United States Patent
Pantin et al.

(10) Patent No.: US 8,734,388 B2
(45) Date of Patent: May 27, 2014

(54) CATHETER FOR MINIMALLY INVASIVE CARDIAC PACING SURGERY AND METHOD OF USE

(75) Inventors: Enrique Pantin, Monmouth Junction, NJ (US); Jonathan Kraidin, Millstone Township, NJ (US)

(73) Assignee: Rutgers, The State University Of New Jersey, New Brunswick, NJ (US)

( * ) Notice: Subject to any disclaimer, the term of this patent is extended or adjusted under 35 U.S.C. 154(b) by 0 days.

(21) Appl. No.: 13/437,284

(22) Filed: Apr. 2, 2012

(65) Prior Publication Data
US 2012/0253280 A1 Oct. 4, 2012

Related U.S. Application Data

(60) Provisional application No. 61/470,779, filed on Apr. 1, 2011.

(51) Int. Cl.
*A61M 29/00* (2006.01)

(52) U.S. Cl.
USPC ..................................... 604/96.01

(58) Field of Classification Search
USPC ..................................... 604/96.01
See application file for complete search history.

(56) References Cited

U.S. PATENT DOCUMENTS

| 4,365,639 | A | | 12/1982 | Goldreyer |
| 4,602,645 | A | | 7/1986 | Barrington et al. |
| 4,699,157 | A | | 10/1987 | Shonk |
| 4,759,378 | A | * | 7/1988 | Swendson et al. ............ 607/122 |
| 5,843,132 | A | | 12/1998 | Ilvento |
| 6,540,765 | B1 | * | 4/2003 | Malacoff ...................... 606/194 |

FOREIGN PATENT DOCUMENTS

WO   WO-2009154720 A1   12/2009

* cited by examiner

*Primary Examiner* — Jason Flick
(74) *Attorney, Agent, or Firm* — Fox Rothschild LLP

(57) ABSTRACT

An assembly of a pulmonary venting catheter and a pacing wire disposed therethrough whereby the pacing wire is extended from the distal end of the catheter tube during pacing mode, eliminating the need for exchanging the venting catheter with a pacing catheter to begin pacing after venting. The pacing wire includes a flexible distal end for a first conductor to conductively engage heart tissue after the pacing wire is extended from the catheter distal end; a second conductor, also exposed outside the catheter distal end, completes the circuit. The pacing wire is lockable in unextended and extended positions at the proximal end portion of the assembly. A method for venting and pacing a patient's heart during cardiac surgery is described, which includes retracting the catheter distal end from the pulmonary artery after venting mode, into the right ventricle during pacing mode, whereafter the pacing wire is extended for pacing.

9 Claims, 2 Drawing Sheets

US 8,734,388 B2

CATHETER FOR MINIMALLY INVASIVE CARDIAC PACING SURGERY AND METHOD OF USE

CROSS REFERENCE TO RELATED APPLICATION

This application claims the benefit of U.S. Provisional Application No. 61/470,779 filed Apr. 1, 2011, the disclosure of which is incorporated herein by reference in its entirety.

FIELD OF THE INVENTION

The present invention relates to the field of cardiac surgery, and more particularly, to a catheter used for minimally invasive cardiac surgery and cardiac pacing during and after the surgery, and a method of using same for treatment of a patient undergoing cardiopulmonary bypass surgery.

BACKGROUND OF THE INVENTION

Minimally invasive cardiac surgery entails the performance of heart surgery through very small incisions. Due to the limited size of the incisions, the patient's heart is not completely exposed. To assure a good or stable heart rhythm during and or after heart surgery, temporary pacing wires, which electrically stimulate the heart, are often sewn to the heart surface, and are used until patient self-pacing is achieved. This can be very difficult to do in some types of minimally invasive cardiac surgery cases without increasing the amount of heart dissection that is done, or increasing the risk of bleeding due to wire placement.

Minimally invasive cardiac surgery is known to utilize catheters that are placed into and along the patient's vasculature to allow safe initiation of cardiopulmonary bypass through catheters via small incisions. During cardiopulmonary bypass, blood is removed from the patient's pulmonary artery and the heart is stopped. The aspirated blood is then oxygenated by a medical apparatus and is then returned to the patient's arterial system at an appropriate location spaced from the heart, such as into a peripheral artery. Once the patient's heart function is undertaken by the cardiopulmonary bypass machine, the surgery can be safely performed through small incisions. The bypass procedure generally utilizes, along with several other catheters, a pulmonary venting (draining) catheter that is placed into and through the vasculature, preferably the jugular vein and superior vena cava, into and through the heart's right atrium and right ventricle, and into the pulmonary artery. The catheter distal end is then left in the pulmonary artery so that drainage of blood is by way of the distally open intake lumen of the catheter. One such pulmonary venting catheter is the ENDOVENT® catheter manufactured by Edwards Lifesciences Corp. (Irvine, Calif.).

It is known to provide a pacing wire into a patient where the distal wire end does not require sewing the tip to heart tissue. By use of a Swan-Ganz PACEPORT® pacing wire manufactured by Edwards Lifesciences Corp., a bipolar pacing wire is introduced into the patient's vasculature and the distal pacing wire end enters into the heart's right ventricle until it becomes engaged against the inner surface of the ventricle, termed intracardiac pacing. This catheter is utilized after pulmonary venting has been performed and after the venting catheter has been withdrawn from the patient. The bipolar pacing wire includes two conductive electrodes that are insulated from each other, one of which extends to the distal wire end, while the other concludes proximally of the distal wire end and is exposed to engage nearby right ventricle tissue. The distal wire end portion is so made to be extremely flexible so as not to damage the heart (or other) tissue of the patient, whereby a length of the distal end portion lies along and against the heart surface for best results. Such intracardiac pacing is performed during weaning from cardiopulmonary bypass, and also for post-operative management to improve cardiac output.

Generally, in the course of performing minimally invasive cardiac surgery without the use of pacing wires sewn to the patient's heart, the pulmonary vent must be exchanged with a pacing catheter that contains the pacing wire through the use of an introducing catheter. This requires a sterile technique with limited access to the head and neck of the patient during the procedure. Additionally, the heart may not have adequate flow or any native activity, making it a challenge to advance the pacing catheter into the right ventricle, and further out into the pulmonary artery. This may lead to numerous problems, including: the catheter being positioned in an incorrect location; the introducing catheter may become bent during the exchange, trapping the pacing catheter; or, the pacing catheter may loop, knot, perforate the heart, damage the heart valves, or become entangled in the chordae tendinae, etc.

It would be desirable to have a catheter assembly and a method of use of same that simplifies the minimally invasive cardiac surgery procedure, reduces the total time needed therefor in patients, and eliminates the need for additional heart surface stitches, among other desirable features, as described herein.

SUMMARY OF THE INVENTION

In one aspect, the present invention is directed in part to a medical apparatus for use during cardiopulmonary bypass surgery of a patient. The medical apparatus includes a venting catheter having a flexible elongate shaft with a distal end, a proximal end, and an inner venting lumen. The inner venting lumen extends from the proximal end of the shaft to an inlet port at the distal end of the shaft. The inlet port is configured to withdraw blood from a pulmonary artery of the patient. The shaft has a length that allows the distal end to be positioned in the pulmonary artery with the proximal end extending transluminally to a central vein and out of the patient through a puncture in the central vein. The medical apparatus also includes a pacing wire disposed within the shaft, and in certain embodiments, the pacing wire may be disposed within the inner venting lumen. The pacing wire is movable axially along the shaft between a first, retracted position and a second, extended position.

The medical apparatus is insertable into the vasculature and heart of a patient for pulmonary venting in a venting mode. During venting mode, the entire pacing wire is within the venting lumen of the catheter tube at the first position. The medical apparatus is also used for pacing of the heart in a pacing mode subsequent to the venting mode. During pacing mode, the pacing wire is extended from the venting lumen of the catheter tube to the second position to engage intracardial tissue of the heart for pacing thereof.

The medical apparatus of the present invention may further include an inflatable balloon having an interior mounted at the distal end of the shaft. The venting catheter may further have an inflation lumen extending from the proximal end to an opening near the distal end in communication with the interior of the balloon.

The pacing wire may include a distal end portion that is flexible and resilient along its length. This distal end portion may include a flexible electrode that is exposed when the pacing wire is in the second position whereby current can be passed between said electrode and the heart. The distal end portion may further include a flexible region located adjacent to and proximally of the flexible electrode. The flexibility of this region tapers as the region extends proximally. The pacing wire may also include a section being wound into a coil to form the flexible region and at least a part of the flexible electrode. The axial spacing between the turns of the coil at the flexible region may increase as the flexible region extends proximally. Additionally, the wire may have a progressively increasing cross-sectional area as the wire extends proximally in the flexible region. The pacing wire can also include at last one marking to indicate the axial position of the pacing wire within the shaft. The pacing wire may further include a proximal electrode spaced proximally from the flexible electrode. This proximal electrode may be formed from a region of a conductive wire having a plurality of coils.

In another aspect, the present invention is directed in part to a method for treatment of a patient undergoing cardiopulmonary bypass surgery. The method includes the steps of: (1) providing an apparatus having a venting catheter assembly including a flexible catheter tube having a distal end, a proximal end, and an inner venting lumen extending from the proximal end to an inlet port at the distal end configured to withdraw blood from a pulmonary artery, and further including a pacing wire within the catheter tube extending to a distal wire end, the pacing wire being movable axially within and along the catheter tube between first and second positions; (2) inserting a distal portion of the catheter tube into the vasculature and into the heart of a patient such that the catheter tube distal end accesses the pulmonary artery; (3) venting the pulmonary artery during cardiopulmonary bypass; (4) closing the venting lumen at a vent port at the catheter tube proximal end; (5) partially retracting the catheter tube distal end from the pulmonary artery and into the heart; (6) extending the distal wire end distally from the catheter tube distal end until a conductive end of the pacing wire enters into conductive engagement with an inner surface of the heart; and (7) pacing the heart.

The apparatus and method of the present invention eliminates the need to utilize a dedicated catheter for delivery of the pacing wire to the heart, thus substantially hastening the initiation of pacing, greatly simplifying the cardiac surgery procedure, reducing the total time, and also reducing risk to the patient. It also permits the surgeon to initiate pacing when the surgeon is unable to exchange catheters due to unusual problems. The present invention eliminates the need for exchanging the venting catheter for the pacing catheter near or at the end of surgery, and eliminates the risk of problems commonly encountered during catheter exchange, such as inadequate blood flow that challenges proper advancement of the pacing catheter into the right ventricle, cardiac perforation or laceration, or post-operative bleeding related to wire placement or removal. It also eliminates, with respect to the pacing catheter, encountering the risks involved during insertion of any catheter through a catheter introducer or into and along the vasculature to and into the heart.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention.

DETAILED DESCRIPTION OF THE INVENTION

Figure 1:
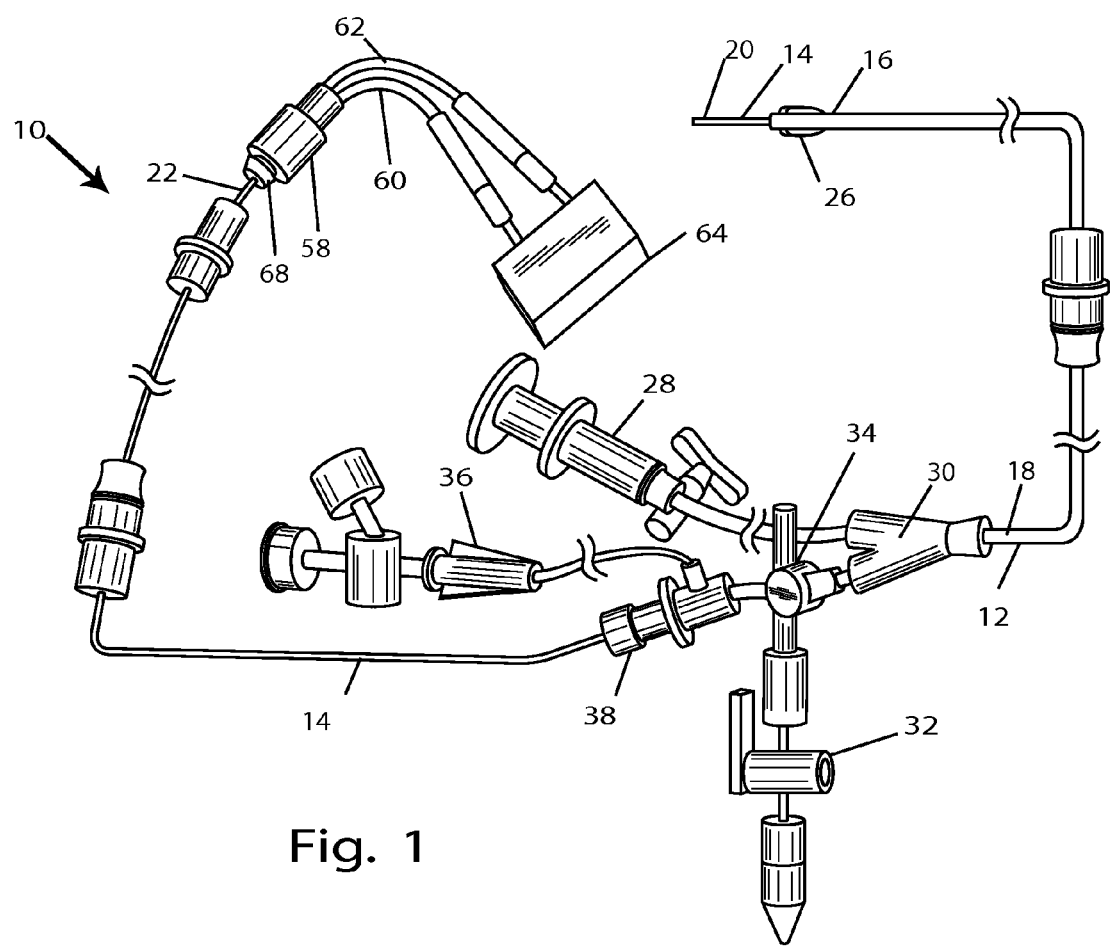
FIG. 1 is a plan view of a pulmonary venting catheter assembly containing a pacing wire, in accordance with the present invention.

In the drawings, like numerals indicate like elements throughout. Certain terminology is used herein for convenience only and is not to be taken as a limitation on the present invention. The terms "proximal" and "distal" refer, respectively, to directions closer to and away from the operator of the apparatus of the present invention. The terminology includes the words specifically mentioned, derivatives thereof, and words of similar import. The terms and expressions used herein, and the embodiments illustrated below, are not intended to be exhaustive or to limit the invention to the precise form disclosed. These terms, expressions and embodiments are chosen and described to best explain the principle of the invention and its application and practical use and to enable others skilled in the art to best utilize the invention.

FIG. 1 illustrates a pulmonary venting catheter assembly 10, including a catheter tube 12 having inserted therethrough a pacing wire 14, in accordance with the present invention. The catheter tube 12 includes a distal end 16 and a proximal end 18. The pacing wire 14 similarly includes a highly flexible distal end portion 20 and a proximal end 22. The illustrated embodiment shows a bipolar catheter setup. The catheter of the present invention may also employ a monopolar scheme, which requires that the patient is appropriately grounded.

As shown in FIG. 1, the catheter assembly 10 is preferably provided with an inflatable/deflatable balloon 26 at the distal end 16 of the catheter tube 12. An inflation/deflation lumen (not shown) extends through catheter tube 12 from balloon 26 to the proximal end 18 of the catheter tube 12, where an inflation/deflation port 28 is provided, joining the catheter tube 12 at a hub 30. The balloon 26 is inflated by injecting air through the inflation port 28, which communicates with the inflation lumen.

Additionally, a controllable vent port 32 is attached to the proximal catheter portion 18 for aspirating blood from the pulmonary artery during cardiopulmonary bypass. A three-way stopcock 34 is placed in the proximal end proximally of hub 30, which serves as a T-piece for both venting and the entry of the pacing wire 14 into the catheter tube 12. Proximally of the stopcock 34 is a pressure tubing 36 that can connect to a pressure sensing line, by which blood pressure in the pulmonary artery is monitored. Just proximally of the connection of the pressure tubing 36 to the catheter assembly 10 is provided a valve 38 that serves to occlusively seal around the pacing wire 14 when the valve 38 is tightened, and also to lock and unlock the axial positioning of the pacing wire 14 with respect to the catheter tube 12. Sterile sheathing may be used around the pacing wire and the catheter tube.

Figure 2:
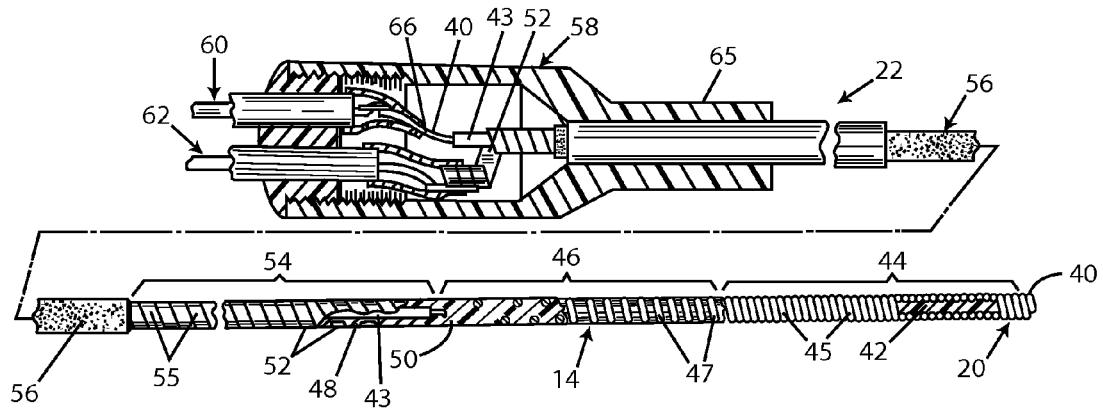
FIG. 2 is a side elevational view partially in section of a pacing wire of the assembly of FIG. 1.

Referring now to FIG. 2, the bipolar pacing wire 14 is shown in greater detail in which the highly flexible distal end portion 20 is shown to include a first conductor 40. The first conductor 40 may have a circular cross-section, and is in the form of an elongated wire having a first section 66 extending from a housing 58 axially through a body 60, a transition section 46 and a distal-most portion 44. As best shown in FIG. 2, the first section 66 is straight and is covered by an insulation cover 43. The transition section 46 comprises a plurality of coils 47 which are spaced apart axially, with the axial spacing between adjacent coils 47 progressively reducing as the transition section 46 extends distally. This progressive reduction is preferred, but not essential. The distal most portion 44 comprises a plurality of contiguous coils 45 and terminates at the distal end 20 of the pacing wire 14. The coils 45, 47 are wound about an insulative core 42. These coils 45, 47 can be tightly or loosely wound to further control the flexibility of the pacing wire 14.

A second conductor 52 concludes at the proximal end 50 of the transition section 46 and extends proximally thereof, being preferably flat and ribbon-shaped in cross-section and being wound about an insulative core section 48 to the proximal end 22 of the pacing wire 14 in the form of contiguous coils 55, being exposed in a coaxial section 54 of the pacing wire 14. This exposed coaxial section 54 forms a proximal electrode. Proximally of the coaxial section 54, the pacing wire 14 is sheathed in an insulative covering 56 until concluding in a housing 58, wherein the first and second conductors 40, 52 are exposed at the end of the pacing wire 14 to be connected to respective leads 60, 62 of a pulse generating apparatus 64.

In the illustrated embodiment, a non-conductive elastomer fills the central space within the coils 55, 47, 45, forming the insulative core sections 42, 48 about which the first and second conductors 40, 52 are wound about, and helping insulate the first conductor 40 from the second conductor 52. In this embodiment, the presence of the elastomer does not alter the flexibility characteristics of the pacing wire 14. In addition to forming the insulative core sections 42, 48, the elastomer encases the coils 47 of the transition section 46 so that only the coils 45 of the distal-most portion 44 of the first conductor are exposed to define a distal electrode. In embodiments where an elastomer is not used, it is preferred to encase the coils 47 of the transition section 46 in a suitable insulation jacket.

Figure 4:
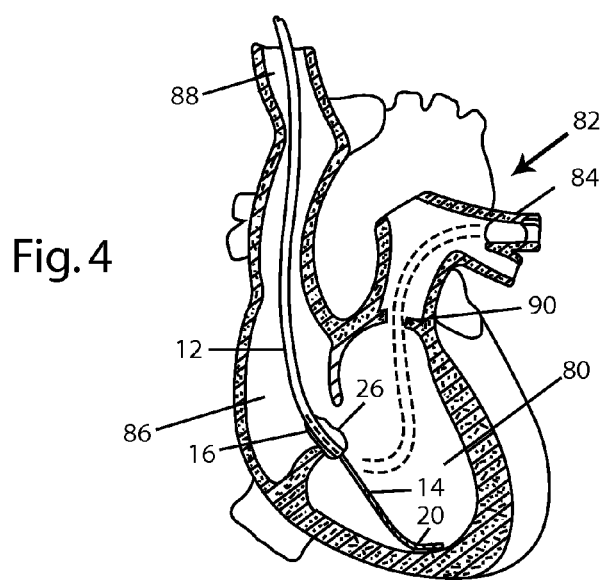
FIG. 4 is a diagrammatic view of the distal portion of the venting catheter illustrating the pacing wire extending from the catheter distal end and in engagement with the inner surface of the right ventricle, with a previous pulmonary venting position shown in dashed lines.

The coaxial section 54, the transition section 46, and the distal most portion 44 comprise that portion of the pacing wire 14, as shown in FIG. 4, that extends from the distal end 16 of the catheter tube 12 when the medical apparatus of the present invention is being used in pacing mode. Specifically, it is the exposed area of the distal most portion 44 that forms the electrode that engages the inner surface of the right ventricle 80 and pace the heart 82.

Figure 3:
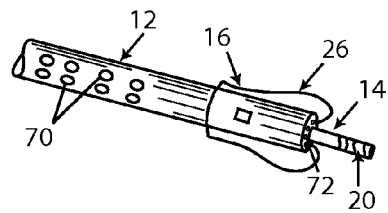
FIG. 3 is an isometric view of the distal pacing wire end extending from the distal end of the venting catheter assembly of FIG. 1.

When the assembly is in venting mode, the distal end 20 of the pacing wire 14 is preferably flush or coterminus with the distal end 16 of the catheter tube 12. FIG. 3 illustrates the highly flexible distal end 20 of the pacing wire 14 being projected to some extent beyond the distal end 16 of catheter tube 12 (shown with the balloon 26 deflated and transparent to reveal detail). It is seen that the pacing wire 14 would not interfere with venting through the catheter tube 12 were it in venting mode (which is shown in dashed lines in FIG. 4). Also seen are a plurality of side ports 70 provided at the distal end 16 of the catheter tube 12 that communicate with the venting lumen 72 there within.

In venting mode, the catheter tube 12 is introduced into a central vein by a percutaneous technique such as the Seldinger technique. The catheter tube 12 is advanced through the central vein and through a vena cava 88 into the right atrium 86 of the heart 82. The balloon 26 on the distal end 16 of the catheter tube 12 is then expanded. As the operator pushes distally on the proximal end of the venting catheter, the flow of blood through the right side of the heart 82 will tend to guide the distal end 16 and the expanded balloon 26 from the right atrium 86 through the tricuspid valve into the right ventricle 80, and from the right ventricle 80 through the pulmonary valve 90 into the pulmonary artery 84. The catheter tube 12 is advanced until the distal end 16 and the inlet ports 70 are positioned in the pulmonary artery 84 downstream of the pulmonary valve 90. Pressure monitoring through pressure ports (not shown) located at the distal end 16 of the catheter tube 12 in communication with the pressure tubing 36 facilitates proper positioning of the distal end 16 in the pulmonary artery 84. Accurate placement may be verified by fluoroscopy or by transesophageal echocardiography. The balloon 26 may then be deflated. Generally, the balloon 26 is used only to help the catheter tube 12 migrate into the pulmonary artery with direction provided by the patient's native blood flow. The balloon 26 should not remain inflated or continue to occlude the pulmonary artery. Leaving the balloon 26 inflated could risk causing pulmonary artery or branch rupture, or lung infarction.

Once in position, and upon starting cardiopulmonary bypass, the blood present in the pulmonary trunk may be vented through the venting lumen 70 of the catheter tube 12 where it is discharged through the proximal end 18 of the catheter tube 12, which extends outside of the patient. The blood withdrawn through the venting catheter tube 12 then travels through the vent port 32 and may be routed to a cardiopulmonary bypass unit for oxygenation and return to the patient's arterial system through an arterial return catheter (not shown).

FIG. 4 illustrates the distal end 16 of the pulmonary venting catheter assembly 10 of the present invention in position within the right ventricle 80 of heart 82 and in pacing mode after venting mode is completed. The catheter tube 12 is shown having been retracted from its position when in venting mode, which is shown in dashed lines extending through the right ventricle 80 and into the pulmonary artery 84 where the balloon 26 had been inflated to occlude the artery. After retraction, the position of the distal end 16 of the catheter tube 12 is about one to three centimeters into the right ventricle 80 from the right atrium 86. The distal end 20 of the pacing wire 14 is shown deployed into its extended position, protruding from the distal end 16 of the catheter tube 12 until it is in engagement with the inner surface of the right ventricle 80 so that the distal electrode located at the distal most portion 44 of the pacing wire 14 of the first conductor 40 can convey a pacing pulse directly to the heart tissue. Proximally of the distal electrode is the proximal electrode formed by the exposed second conductor 52, by which the circuit is completed via heart tissue and bodily fluids. The catheter tube 12 is seen extending proximally through the right atrium 86 and the superior vena cava 88 into the patient's vasculature.

It is preferable that the catheter tube 12 be marked on its exposed proximal end portion 18 such that the operator may determine the precise distance between the distal end 16 of the catheter tube 12 when in position for venting mode and when in position for pacing mode, so that retraction is quickly attained during the surgical procedure. This may easily be determined by ultrasound guidance prior to venting mode. When the catheter assembly 10 is in venting mode, the axial position of the pacing wire 14 within the catheter tube 12 is locked such that the distal end 40 of the pacing wire is approximately coterminus with the distal end 16 of catheter tube 12. It is likewise preferable that the exposed portion of the proximal end of the pacing wire 14 be marked to indicate the amount by which the pacing wire 14 is to be extended from the distal end 16 of the catheter tube 12 to engagement with the inner surface of the right ventricle 80, after which the pacing wire 14 will again be locked, for pacing mode. Axial positioning of the pacing wire 14 is attained at valve/lock 38 in the proximal end of the catheter assembly 10, as provided hereinabove with respect to FIG. 1.

Tests have shown that the venting/pacing catheter assembly of the present invention is easily operable by the operator to convert from venting mode to pacing mode, which can be performed within two minutes, because exchange of catheters is eliminated.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical apparatus for use during cardiopulmonary bypass surgery of a patient, comprising:
    a venting catheter comprising a flexible elongate shaft having a distal end, a proximal end, and an inner venting lumen, the proximal end including a valve assembly controllable between a vent port and a sealing wire valve, the inner venting lumen extending from the valve assembly at the proximal end to an inlet port at the distal end of the shaft and configured to withdraw blood from a pulmonary artery, the shaft having a length selected to allow the distal end to be positioned in the pulmonary artery with the proximal end extending transluminally to a central vein and out of the patient through a puncture in the central vein;
    a pacing wire disposed through the sealing wire valve and within said shaft and being movable axially therealong between a first, retracted position and a second, extended position;
    wherein the apparatus is insertable into the vasculature and heart of a patient for pulmonary venting in a venting mode, during which the pacing wire is within the venting lumen of the catheter tube at the first position, and for pacing of the heart in a pacing mode, during which the pacing wire is extended from the distal end of the shaft to the second position to engage intracardial tissue of the heart for pacing thereof.

2. The medical apparatus of claim 1 further comprising an inflatable balloon having an interior mounted at the distal end of the shaft.

3. The medical apparatus of claim 1, wherein the pacing wire is disposed within the inner venting lumen.

4. The medical apparatus of claim 1, wherein the pacing wire comprises:
    a distal end portion that is flexible and resilient along its length, the distal end portion having a flexible electrode that is exposed when the pacing wire is in the second position whereby current can be passed between the electrode and the heart, and further comprising a flexible region located adjacent to and proximally of the flexible electrode with the flexibility of the region tapering as the region extends proximally; and
    a length of wire conductor being wound into a coil to from the flexible region and at least a part of the flexible electrode.

5. The medical apparatus of claim 4, wherein an axial spacing between turns of the coil at the flexible region increases as the flexible region extends proximally.

6. The medical apparatus of claim 4, wherein the pacing wire further comprises a proximal electrode spaced proximally from the flexible electrode.

7. The medical apparatus of claim 6, wherein the pacing wire further comprises a conductive wire having a plurality of coils in which a region of the coils are exposed to define the proximal electrode.

8. A method for treatment of a patient undergoing cardiopulmonary bypass surgery, comprising the steps of:
    inserting a distal portion of the catheter shaft of the medical device of claim 1 into the vasculature and into the heart of a patient such that the catheter shaft distal end accesses the pulmonary artery;
    venting the pulmonary artery during cardiopulmonary bypass;
    closing the venting lumen at the inlet port at the catheter shaft proximal end;
    partially retracting the catheter shaft distal end from the pulmonary artery and into the heart;
    extending the pacing wire distally from the catheter shaft distal end until a conductive end of the pacing wire enters into conductive engagement with an inner surface of the heart; and
    pacing the heart.

9. The medical apparatus of claim 1, wherein said inlet port at said distal end of said shaft of said venting catheter comprises a plurality of side ports that communicate with said inner venting lumen.

\* \* \* \* \*